United States Patent
Wang et al.

(10) Patent No.: US 10,639,425 B2
(45) Date of Patent: May 5, 2020

(54) SYRINGE, AND DEVICE FOR RAPIDLY LOADING AND RELEASING THE SAME

(71) Applicant: Suzhou Hengrui Disheng Medical Co., Ltd, Suzhou (CN)

(72) Inventors: Jun Wang, Suzhou (CN); Guofeng Kan, Suzhou (CN); Pengcheng Long, Suzhou (CN)

(73) Assignee: SUZHOU HENGRUI DISHENG MEDICAL CO., LTD., Suzhou (CN)

( * ) Notice: Subject to any disclaimer, the term of this patent is extended or adjusted under 35 U.S.C. 154(b) by 229 days.

(21) Appl. No.: 15/825,853

(22) Filed: Nov. 29, 2017

(65) Prior Publication Data

US 2018/0304016 A1      Oct. 25, 2018

(30) Foreign Application Priority Data

Apr. 21, 2017   (CN) .......................... 2017 1 0268908 4
Apr. 21, 2017   (CN) ................... 2017 2 0429593 2 U

(51) Int. Cl.
  *A61M 5/20*      (2006.01)
  *A61M 5/145*     (2006.01)
(52) U.S. Cl.
  CPC ...... *A61M 5/2033* (2013.01); *A61M 5/14546* (2013.01); *A61M 2005/14573* (2013.01); *A61M 2005/2073* (2013.01)
(58) Field of Classification Search
  CPC ........ A61M 5/2033; A61M 2005/2073; A61M 2039/1077; A61M 5/14546; A61M 2005/2488; A61M 2005/14573

USPC ......................................................... 604/134
See application file for complete search history.

(56) References Cited

U.S. PATENT DOCUMENTS

| | | | | |
|---|---|---|---|---|
| 6,336,913 B1 * | 1/2002 | Spohn | ............... | A61M 5/14546 604/154 |
| 2001/0047153 A1 * | 11/2001 | Trocki | .............. | A61M 5/14546 604/155 |
| 2009/0156931 A1 * | 6/2009 | Nemoto | ............ | A61M 5/14546 600/432 |

\* cited by examiner

*Primary Examiner* — Bhisma Mehta
*Assistant Examiner* — Nidah M Hussain
(74) *Attorney, Agent, or Firm* — Muncy, Geissler, Olds & Lowe, P.C.

(57) ABSTRACT

A device for rapidly loading and releasing a syringe. A limiting flange and clamping flange are on an outer side wall of an end, connected to the device, of the syringe. The clamping flange is close to a rear end of the syringe. The device includes an injection head. An outer collar, middle plate, and inner collar are sequentially inside the injection head. The outer collar includes an upper and lower part that are disposed up and down. The inner collar includes an upper part of the inner collar and a lower part of the inner collar that are disposed up and down. Elastic structures are between the upper part of the inner collar and injection head and between the lower part of the inner collar and injection head. The injector syringe can be loaded onto the device and taken out rapidly if the syringe is rotated.

13 Claims, 10 Drawing Sheets

SYRINGE, AND DEVICE FOR RAPIDLY LOADING AND RELEASING THE SAME

TECHNICAL FIELD

The present disclosure relates to the technical field of injector syringe design, and more particularly, relates to a device for rapidly loading and releasing a syringe.

BACKGROUND ART

A syringe is generally used with an injector. The syringe contains liquid. The syringe is connected to the injector, and the injector pushes the liquid in the syringe for injection.

An existing power injector has a problem of inconvenient use regarding loading and releasing of the syringe, which may affect a manner of loading the syringe onto the injector and/or keeping the syringe inside the injector. The inconvenience of the design may complicate the way of loading and releasing for a user (for example, a care provider).

SUMMARY OF THE INVENTION

For the problem in the background art, the present disclosure provides a device for rapidly loading and releasing a syringe, a limiting flange and a clamping flange are disposed on an outer side wall of a connection end of the syringe, the clamping flange is close to a rear end of the connection end of the syringe, and an outer circle of the limiting flange is of an oval shape;
the device includes an injection head, and an outer collar, a middle plate, an inner collar are disposed sequentially inside the injection head; the outer collar includes an upper part of the outer collar and a lower part of the outer collar that are disposed up and down; the inner collar includes an upper part of the inner collar and a lower part of the inner collar that are disposed up and down, and elastic structures are disposed between the upper part of the inner collar and the injection head and between the lower part of the inner collar and the injection head;
during loading, the syringe is inserted into the injection head, the clamping flange passes through the outer collar and the middle plate and then pushes the inner collar away, the upper part of the inner collar moves upwards, and the lower part of the inner collar moves downwards; after the clamping flange passes through the inner collar, under the action of the elastic structures, the upper part of the inner collar and the lower part of the inner collar are restored, a side of the clamping flange abuts on a side of the inner collar, and a side of the limiting flange abuts on the middle plate, so that the syringe is positioned along an axial direction; in this case, the upper part of the outer collar and the lower part of the outer collar are fixed, an inner circle of the outer collar formed by the upper part of the outer collar and the lower part of the outer collar is of an oval shape matching the outer circle of the limiting flange, and the limiting flange is fit into the oval inner circle of the outer collar; and
during releasing, the syringe is rotated, the limiting flange pushes to enable the upper part of the outer collar and the lower part of the outer collar to respectively move upwards and downwards, the upper part of the outer collar and the lower part of the outer collar respectively drive, by means of connection pieces, the upper part of the inner collar and the lower part of the inner collar to move upwards and downwards; the inner collar is opened, the clamping flange is moved outwards to be disengaged from the inner collar, to release the syringe; at the same time, the limiting flange is disengaged from the outer collar, and under the action of the elastic structures, the inner collar and the outer collar are restored.

Preferably, a difference between a major semi axis and a minor semi axis of the outer circle of the limiting flange is greater than a movable distance of the upper part of the outer collar and the lower part of the outer collar.

Preferably, a side of the clamping flange that facing away from the limiting flange is a first ramp, a second ramp is disposed on an inner circle of the inner collar, and when the clamping flange pushes the inner collar away, the first ramp slides along the second ramp.

Preferably, a chamfer is disposed on a side of an inner circle of the outer collar that facing away from the middle plate.

Preferably, the connection pieces include bosses disposed on sides, facing the middle plate, of the upper part of the outer collar and the lower part of the outer collar, first pocket holes are disposed on corresponding locations on the middle plate, second pocket holes are disposed on corresponding locations on the upper part of the inner collar and the lower part of the inner collar, the bosses pass through the first pocket holes and the second pocket holes, and the bosses can move upwards and downwards relative to the first pocket holes and the second pocket holes.

Preferably, before loading, the bosses are close to an inner side of the first pocket holes and close to an outer side of the second pocket holes.

Preferably, an outer circle of the clamping flange is round.

Preferably, a round through hole is disposed at the center of the middle plate, a diameter of the round through hole is greater than an outer diameter of the clamping flange, and is less than a length of a long axis of the outer circle of the limiting flange.

Preferably, a limiting step hole is disposed on a side, facing the syringe, of the injection head, a slot communicate with the limiting step hole is disposed on the other side, and the outer collar, the middle plate, and the inner collar are installed inside the slot.

Preferably, the device further includes a guide sleeve, used to implement connection between the device for rapidly loading and releasing a syringe and an injector.

Preferably, one end of the guide sleeve is connected to the injection head, the other end is connected to the injector; a guide sleeve inner hole is disposed on the guide sleeve along an axial direction, the guide sleeve inner hole is communicated with the inner collar, and the rear end of the connection end of the syringe passes through the inner collar and then stretches into the guide sleeve inner hole.

Preferably, the guide sleeve inner hole is in clearance fit with the outside of the rear end of the connection end of the syringe.

The present disclosure further provides a syringe, characterized in that a limiting flange and a clamping flange are disposed on an outer side wall of an end, connecting to an injector, of the syringe, the clamping flange is close to a rear end of the connection end of the syringe, and an outer circle of the limiting flange is of an oval shape.

Preferably, a side, facing away from the limiting flange, of the clamping flange is a ramp.

By means of the foregoing technical solutions, compared with the prior art, the present disclosure has the following advantages and positive effects:

By means of the device for rapidly loading and releasing a syringe provided in the present disclosure, an injector syringe having a special structure can be rapidly loaded onto the device and taken out as long as the syringe is rotated, so that an operation is convenient, and a structure is simple and compact. In addition, the syringe is connected to the device stably, and does not easily shake, thereby implementing stable connection to an injector.

BRIEF DESCRIPTION OF THE DRAWINGS

The foregoing and other features and advantages may be understood more clearly with reference to the accompany drawings by means of the following detailed descriptions, where.

DETAILED DESCRIPTION OF THE INVENTION

Figure 1:
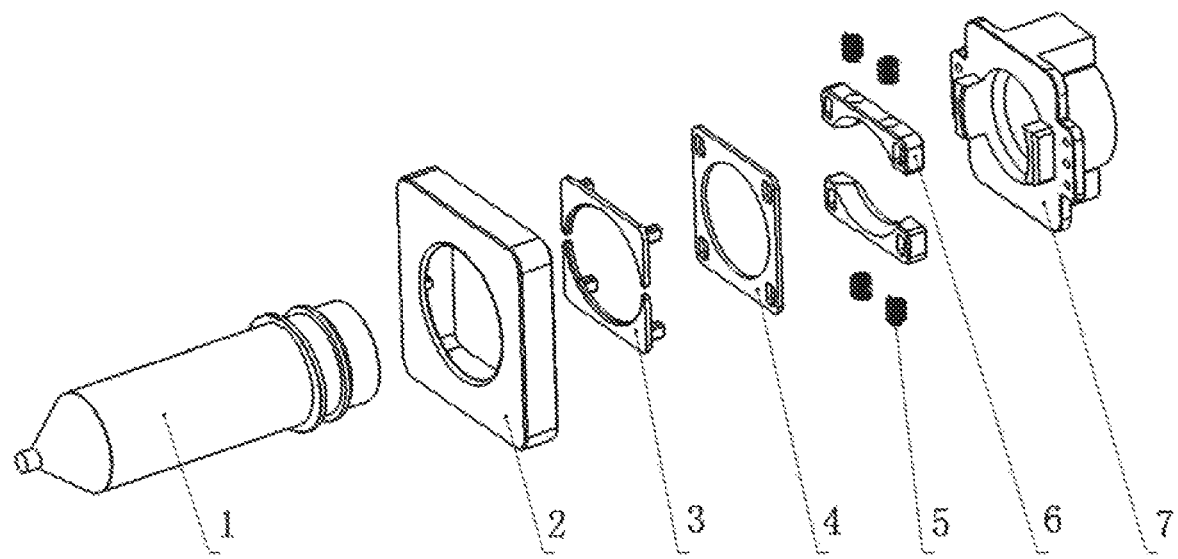
FIG. 1 is a schematic disassembly diagram of a device for rapidly loading and releasing a syringe provided in the present disclosure.

The following describes in detail the present disclosure with reference the accompany drawings of embodiments of the present disclosure. However, the present disclosure may be implemented in multiple different forms, which should not be limited by the embodiments. On the contrary, the embodiments are provided to implement the full and complete disclosure, and to enable a person skilled in the art to fully understand the scope of the present disclosure. In the accompanying drawings, for clarity, sizes and relative sizes of layers and areas may be enlarged.

It should be noted that all direction indications (for example, up, down, left, right, front, and back) in the embodiments of the present disclosure are merely used to explain a relative location relationship between components and moving statuses of the components in a particular posture (as shown in the accompanying drawings), and if the particular posture changes, the direction indications change correspondingly.

Referring to FIG. 1 to FIG. 20, the present disclosure provides a device for rapidly loading and releasing a syringe. A limiting flange 101 and a clamping flange 100 are disposed on an outer side wall of an end, connected to the device, of a syringe, the clamping flange is close to a rear end of the connection end of the injector syringe 1, and an outer circle of the limiting flange 101 is of an oval shape. The device for rapidly loading and releasing a syringe includes an injection head 2, and an outer collar 3, a middle plate 4, an inner collar 6 are disposed sequentially inside the injection head 2. The outer collar 3 includes an upper part of the outer collar and a lower part of the outer collar that are disposed up and down. The inner collar 6 includes an upper part of the inner collar and a lower part of the inner collar that are disposed up and down, and elastic structures are disposed between the upper part of the inner collar and the injection head and between the lower part of the inner collar and the injection head.

During loading of the syringe 1, the rear end of the syringe is inserted into the injection head 2 in any direction, the clamping flange 100 passes through the outer collar 3 and the middle plate 4 and then pushes the inner collar away 6, so that the upper part of the inner collar moves upwards, and the lower part of the inner collar moves downwards. After the clamping flange 100 passes through the inner collar 6, under the action of the elastic structures, the upper part of the inner collar and the lower part of the inner collar are restored, a side of the clamping flange 100 (a plane 1002 of the clamping flange) abuts on a side of the inner collar 6, and a side of the limiting flange 101 abuts on a side of the middle plate 4, so that the syringe 1 is positioned along an axial direction. In this case, the upper part of the outer collar and the lower part of the outer collar are fixed, an inner circle of the outer collar formed by the upper part of the outer collar and the lower part of the outer collar is of an oval shape matching the outer circle of the limiting flange, and the limiting flange 101 is fit into the oval inner circle of the outer collar 3.

During releasing of the syringe 1, the syringe 1 is rotated. Because the outer circle 1011 of the limiting flange 101 and the inner circle 301 of the outer collar 3 are of oval shapes matching each other, when the limiting flange 101 is rotated, the limiting flange 101 pushes to enable the upper part of the outer collar and the lower part of the outer collar to respectively move upwards and downwards, and the upper part of the outer collar and the lower part of the outer collar respectively drive, by means of connection pieces, the upper part of the inner collar and the lower part of the inner collar to move upwards and downwards. The inner collar 6 is separated, so that the clamping flange 100 can be moved out and disengaged from the inner collar, to implement releasing of the syringe. At the same time, the limiting flange 101 is moved out and disengaged from the outer collar 3, and under the action of the elastic structures, the inner collar and the outer collar are restored.

By means of the device for rapidly loading and releasing a syringe provided in the present disclosure, a syringe provided with a limiting flange and a clamping flange can be loaded onto and removed from the device rapidly as long as the syringe is rotated, so that an operation is convenient and a structure is simple and compact. In addition, the syringe is connected to the device stably, and does not shake easily, thereby implementing stable connection to an injector.

In this embodiment, with reference to FIG. 1, FIG. 6, FIG. 7, and FIG. 8, a shape of the injection head 2 is a rectangle. Certainly, in another embodiment, the injection head 2 entirely may be of a disk shape, or the like, which is not limited herein. A round limiting step hole 201 is disposed on a side, facing the syringe 1, of the injection head 2, and the limiting step hole 201 is used for inserting the syringe 1 into the device. A slot 200 communicating with the limiting step hole 201 is disposed on the other side of the injection head 2, and the outer collar 3, the middle plate 4, and the inner collar 6 are vertically disposed inside the slot 200 sequentially. In this embodiment, shapes of the outer collar 3, the middle plate 4, and the inner collar 6 match the slot 200, so that the outer collar, the middle plate, and the inner collar are directly fit into the slot 200, and are limited in the vertical direction. The outer collar 3, the middle plate 4, and the inner collar 6 are vertically disposed and sides abut on each other. At the same time, under the combined action of the side of the slot and the elastic structures, initial locations of the outer collar 3, the middle plate 4, and the inner collar 6 are ensured. Inner circle of the outer collar 3, the middle plate 4, and the inner collar 6 and the limiting step hole 201 are located in a same axial direction. An end of the syringe passes through the limiting step hole 201 and then is inserted into the inner circle of the outer collar 3, the middle plate 4, and the inner collar 6.

In this embodiment, the outer collar 3 and the inner collar 6 are linked inside the slot by means of the connection pieces. The connection pieces include bosses 303 disposed on a side, facing the middle plate 4, of the outer collar.

Figure 7:
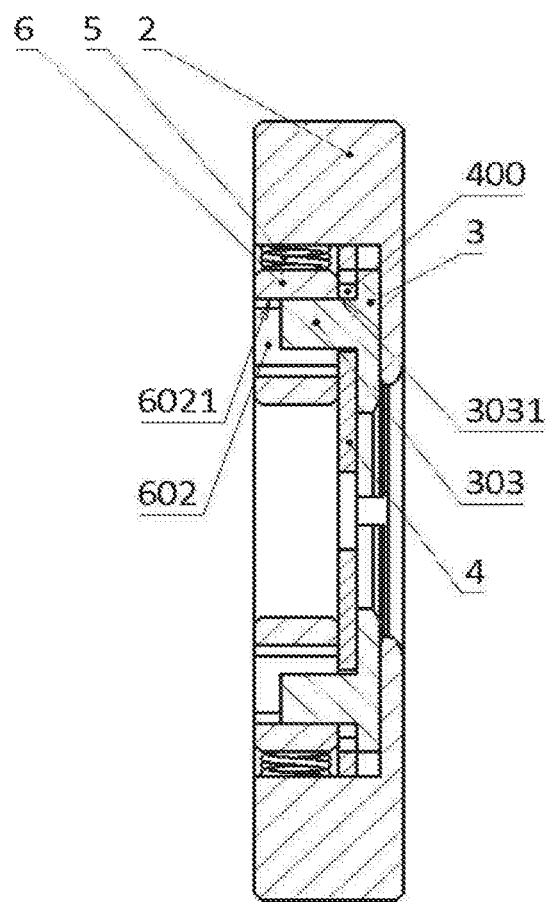
FIG. 7 is a schematic diagram showing location relationships between bosses on an outer collar and first pocket holes on a middle plate and between the bosses and second pocket holes on an inner collar before loading.
Figure 8:
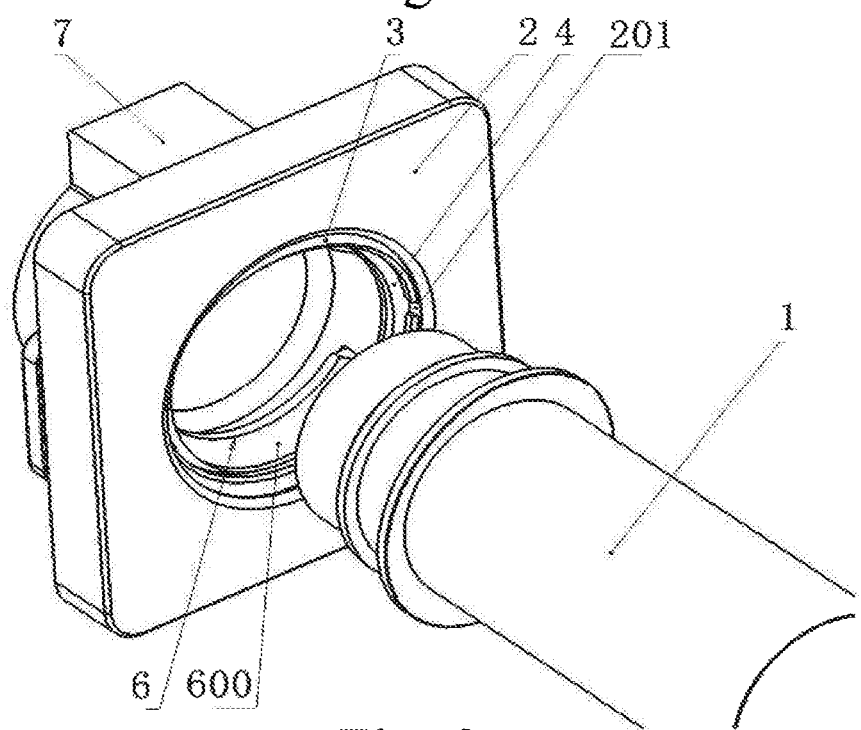
FIG. 8 is schematic diagram of the syringe and the injection head when loading starts.

Specifically, with reference to FIG. 1 and FIG. 7, at least one boss 303 is disposed on a side, facing the middle plate 4, of each of the upper part of the outer collar and the lower part of the outer collar. First pocket holes 400 are disposed on locations, corresponding to the bosses 303, on the middle plate 4, and second pocket holes 602 are respectively disposed on locations, corresponding to the bosses, of the upper part of the inner collar and the lower part of the inner collar. The bosses 303 sequentially pass through the first pocket holes 400 and the second pocket holes 602. Elastic structures 5 are disposed between the top of the upper part of the inner collar and the top of the slot 200, and elastic structures 5 are disposed between the bottom of the lower part of the inner collar and the bottom of the slot 200. The elastic structures 5 may be specifically implemented by using springs or the like, which is not limited herein.

Before the syringe is loaded, the bosses are close to inner sides (that is, sides close to the axial center) of the first pocket holes 400, and at the same time, close to outer sides (that is, sides away from the axial center) of the second pocket holes 602, as shown in FIG. 7. In the present disclosure, the bosses 303 are disposed in a manner of cooperating with the first pocket holes 400 and the second pocket holes 602, so that during loading, when the inner collar 6 is separated, the inner collar does not drive the outer collar 3 to move, and a location of the outer collar 3 remains fixed, and during releasing, when the outer collar 3 is separated, the outer collar drives separation of the inner collar 6.

Further, in this embodiment, the first pocket holes 400 and the second pocket holes 602 are of a vertical strip structure, and provide space for the bosses 303 to move inside the first pocket holes 400 and the second pocket holes 602.

Further, in this embodiment, in order that the upper part of the outer collar and the lower part of the outer collar can move upwards and downwards stably during usage, one boss is disposed on each of two sides of the upper part of the outer collar, one boss is disposed on each of two sides of the lower part of the outer collar, and quantities and locations of the first pocket holes and the second pocket holes correspond to those of the bosses, as shown in FIG. 1. Certainly, in another embodiment, only one boss or multiple bosses may be disposed on each of the upper part of the outer collar and the lower part of the outer collar, which is not limited herein.

In this embodiment, the outer circle 1011 of the limiting flange 101 is of an oval shape. Before and after loading, the inner circle 301 formed by the upper part of the outer collar and the lower part of the outer collar matches the outer circle of the limiting flange 101. A difference between a major semi axis and a minor semi axis of the outer circle of the limiting flange 101 is greater than a removable distance of the upper part of the outer collar and the lower part of the outer collar. In this way, not only it can be ensured the limiting flange 101 is just fit into the inner circle of the outer collar 3 during loading, but also the limiting flange 101 can be rotated and push to separate the outer collar during releasing.

Before and after loading, the outer circle 1011 of the limiting flange may abut on the inner circle 301 of the outer collar, or there may an interval between the outer circle 1011 of the limiting flange and the inner circle 301 of the outer collar, which is not limited herein, as long as the outer collar can be separated when the limiting flange 101 is rotated.

Figure 5:
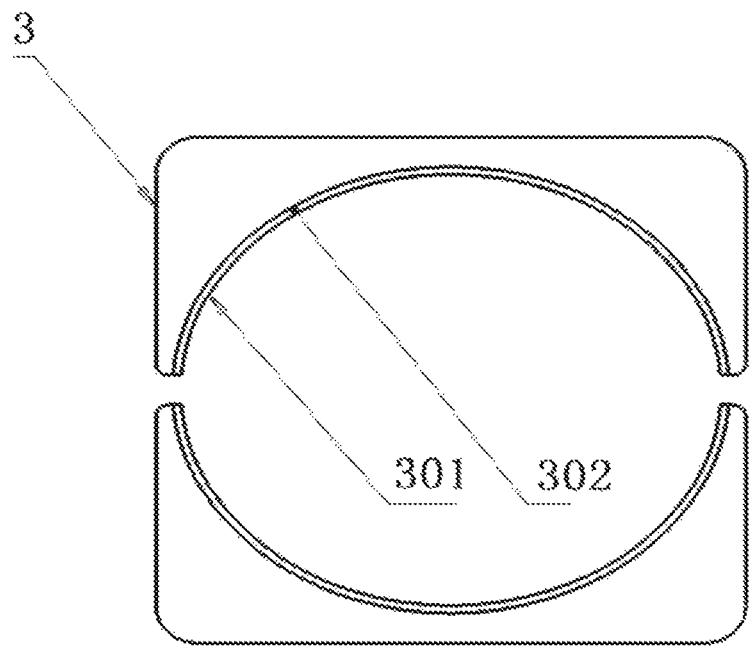
FIG. 5 is a schematic diagram showing that an inner circle formed by an upper part of an outer collar and a lower part of the outer collar is of an oval shape in the present disclosure.
Figure 6:
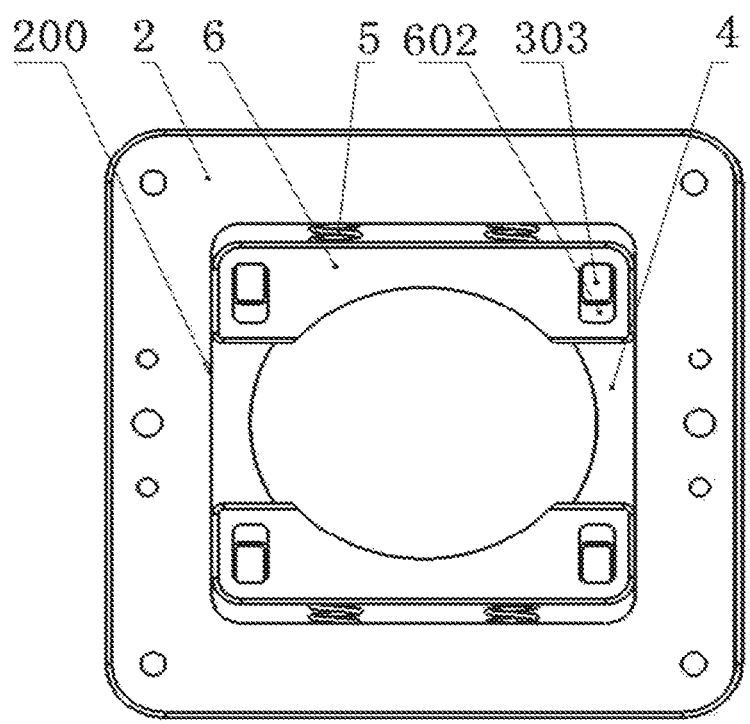
FIG. 6 is a schematic structural diagram of a back of an injection head in the present disclosure.

A chamfer 302 is further disposed on a side, facing away from the middle plate 4, of the inner circle of the outer collar, as shown in FIG. 5. In the present disclosure, by means of the chamfer 302, the limiting flange 101 is more easily fit into the inner circle of the outer collar.

In this embodiment, the outer circle of the clamping flange 100 is round. A maximum distance, along a moving direction, of the inner circle formed by the upper part of the inner collar and the lower part of the inner collar is less than a diameter of the outer circle of the clamping flange 100 in an initial stage, so that a side of the inner collar abuts on a side of the clamping flange to implement limiting along an axial direction.

Figure 9:
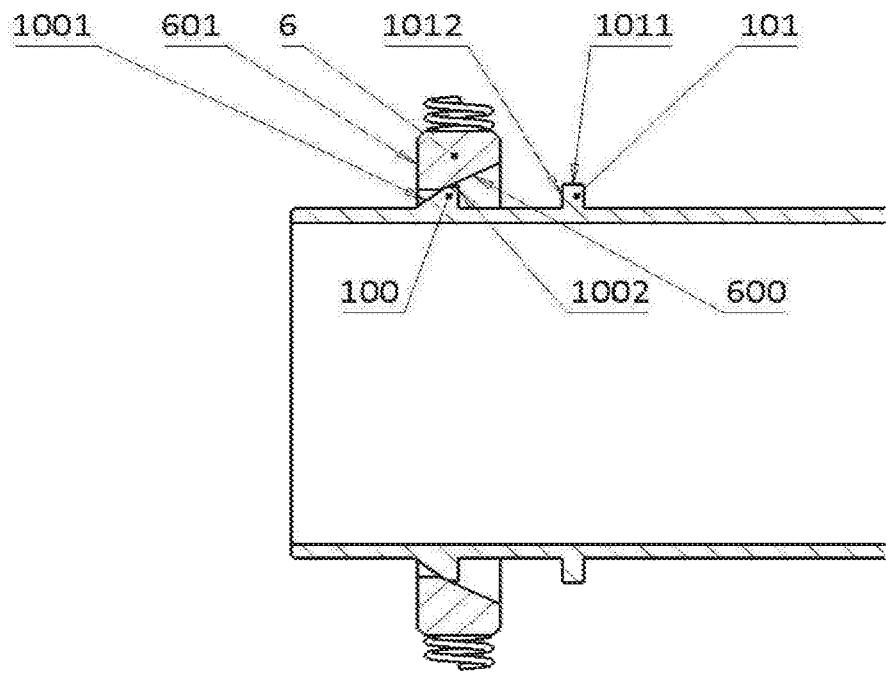
FIG. 9 is a schematic diagram showing that a clamping flange pushes the inner collar away during loading.
Figure 10:
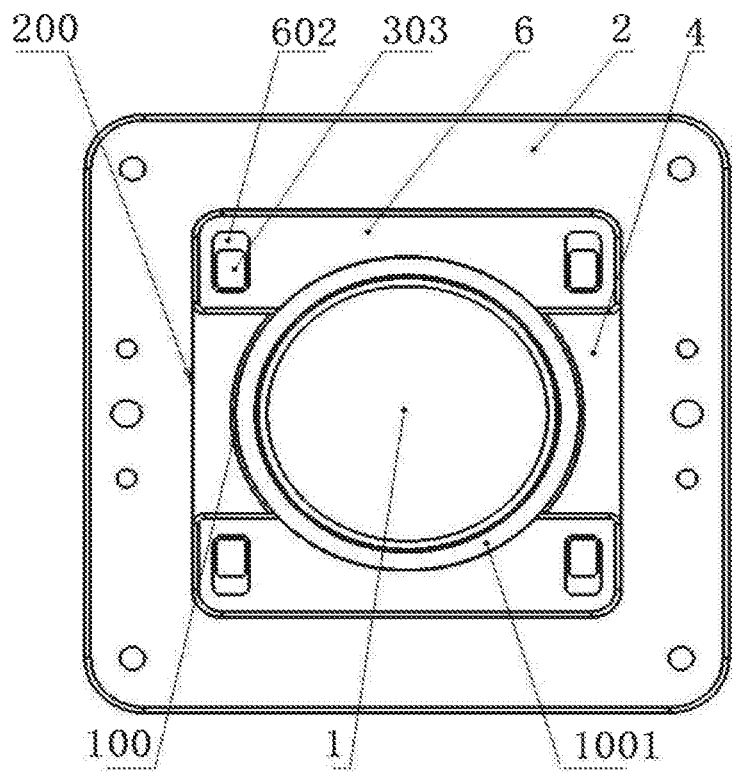
FIG. 10 is a schematic diagram of the back of the injection head when the clamping flange pushes the inner collar away to the maximum during loading.
Figure 11:
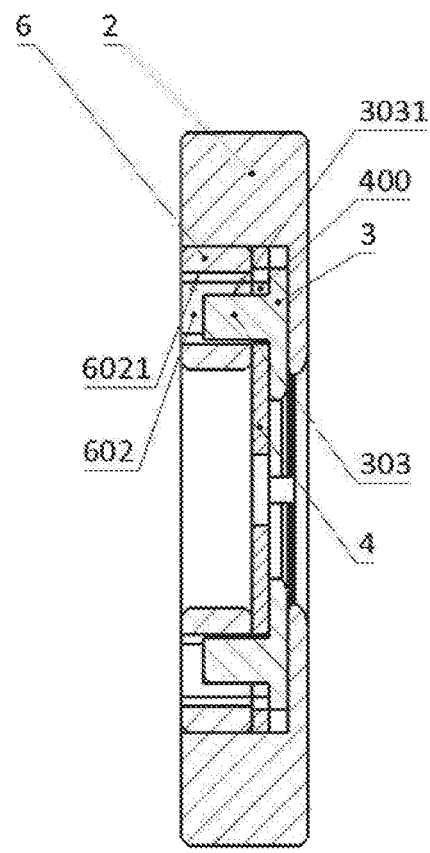
FIG. 11 is a schematic diagram showing location relationships between the bosses on the outer collar and a round through hole on the middle plate and between the bosses and the second pocket holes on the inner collar when the clamping flange pushes the inner collar away to the maximum during loading.
Figure 12:
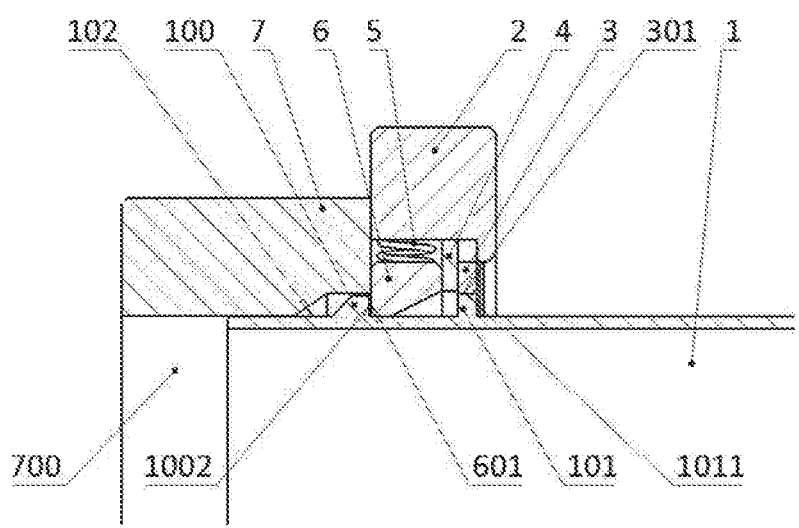
FIG. 12 is a schematic diagram showing a location relationship between components after the syringe is loaded completely.
Figure 13:
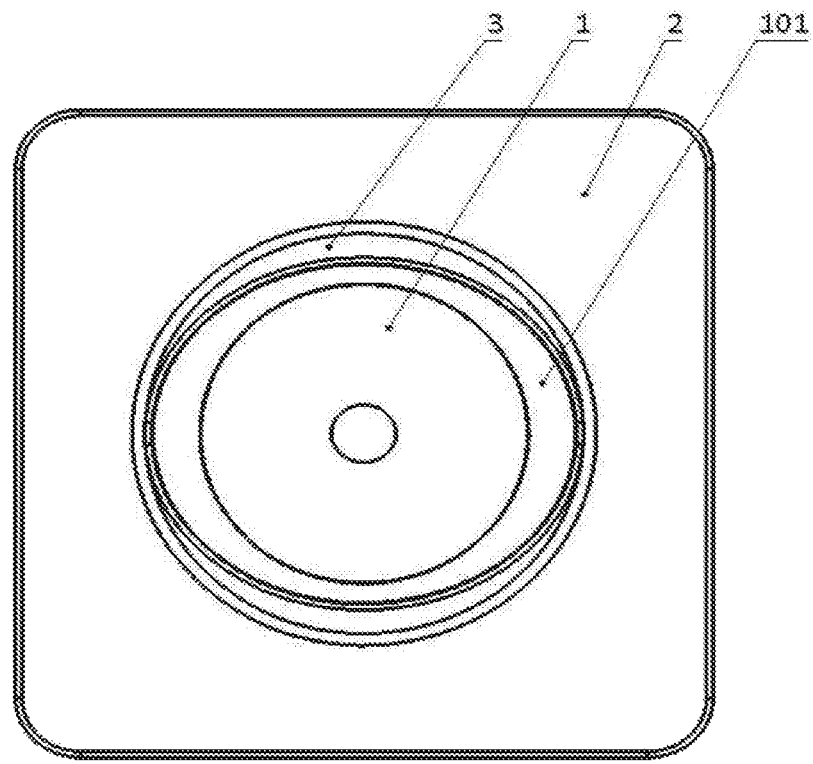
FIG. 13 is a front view of the syringe and a device for rapid loading and releasing the syringe after the injector syringe is loaded completely.
Figure 14:
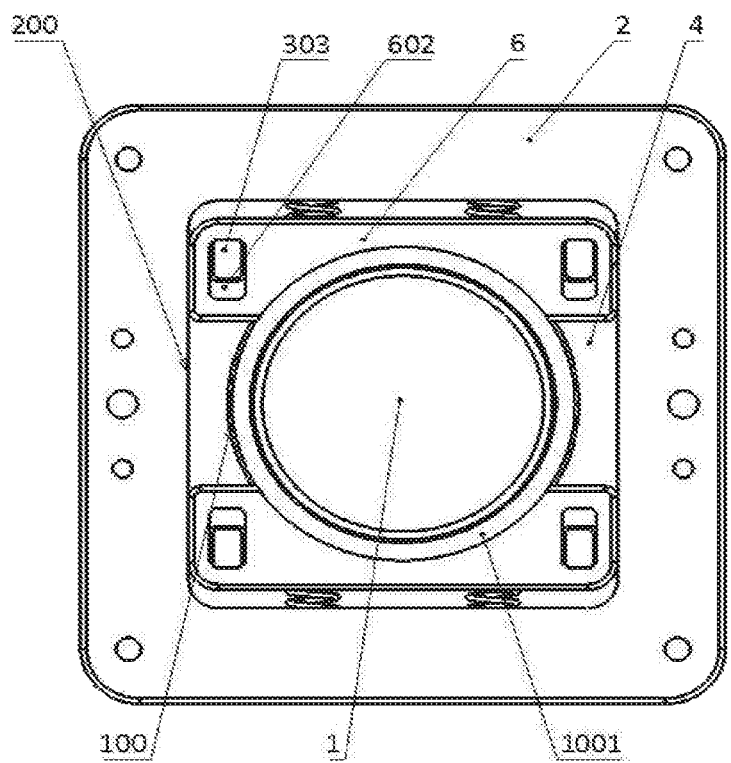
FIG. 14 is a schematic structural diagram of the back of the injection head after the injector syringe is loaded completely.
Figure 15:
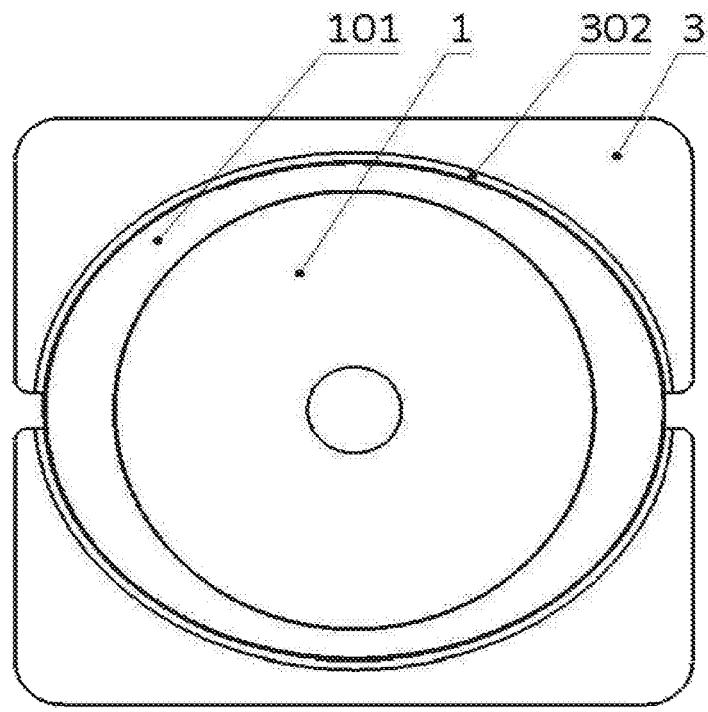
FIG. 15 is a schematic diagram showing a location relationship between the outer collar and the limiting flange after the injector syringe is loaded completely.
Figure 16:
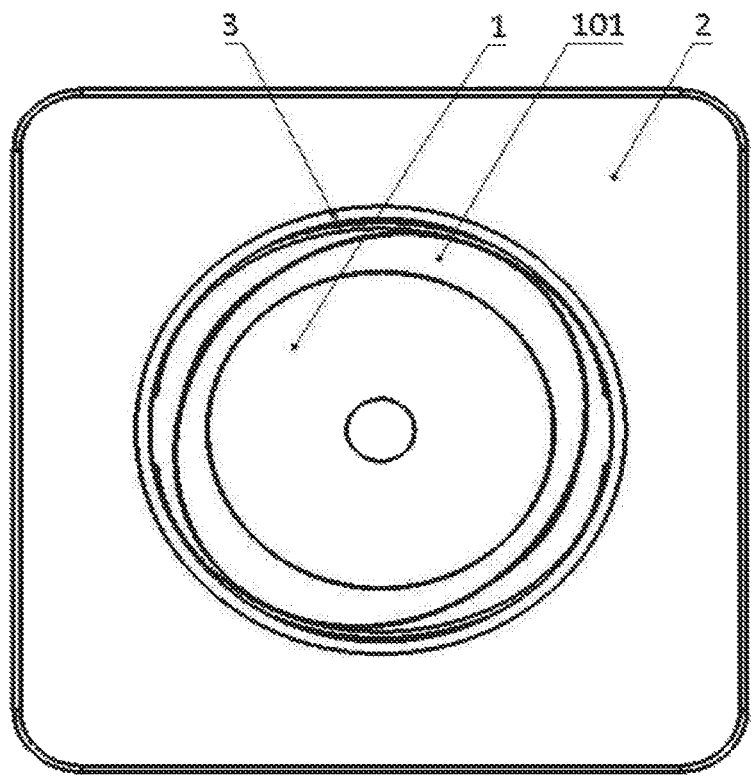
FIG. 16 is a schematic diagram showing that the syringe is rotated to the maximum during releasing of the injector syringe.
Figure 17:
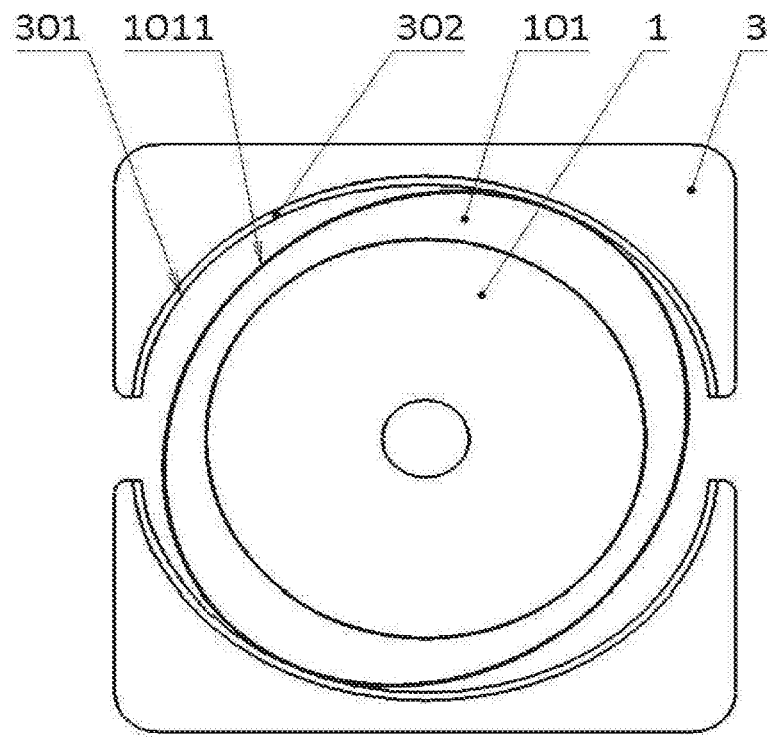
FIG. 17 is a schematic diagram showing a location relationship between the outer collar and the limiting flange during releasing of the injector syringe.
Figure 18:
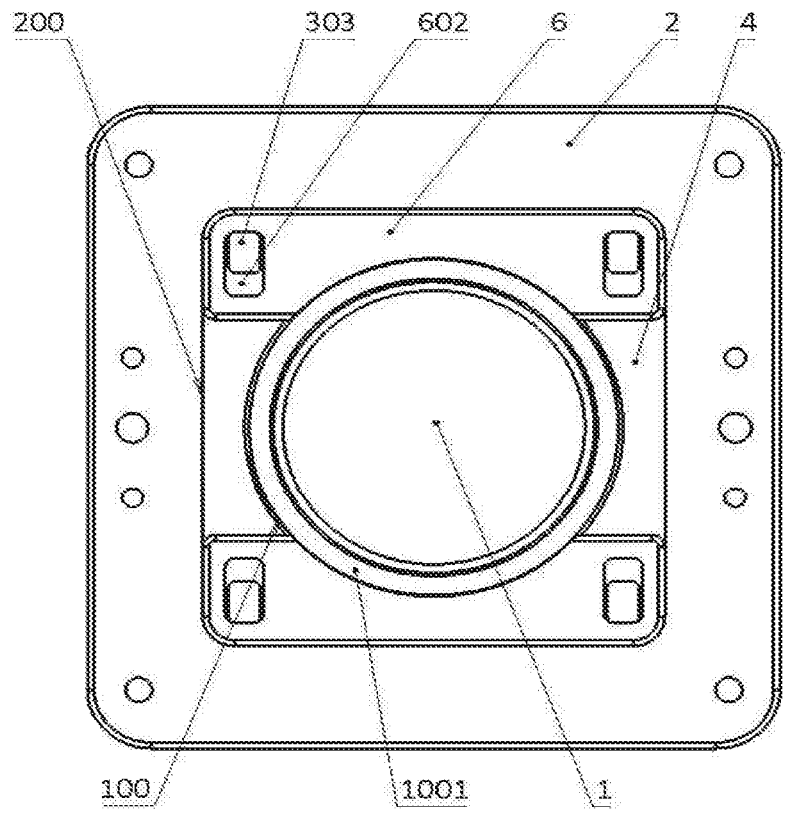
FIG. 18 is a schematic structural diagram of the back of the injection head when the syringe is rotated to the maximum during releasing of the injector syringe.
Figure 19:
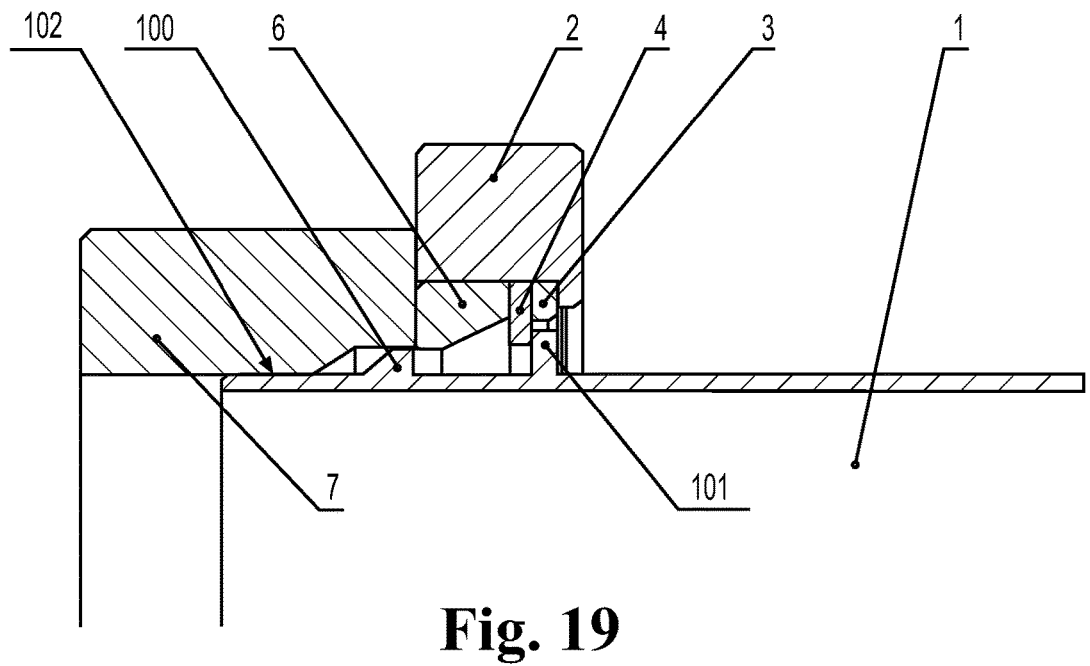
FIG. 19 is a schematic diagram showing a location relationship between components when the syringe is rotated to the maximum during releasing of the injector syringe.
Figure 20:
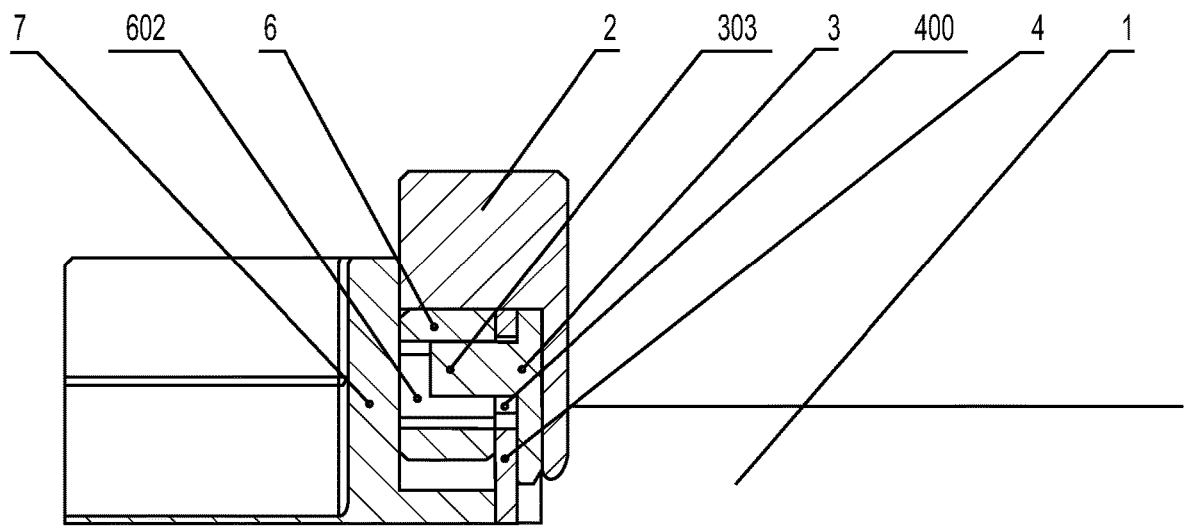
FIG. 20 is a schematic diagram showing a location relationship between the bosses on the outer collar, a round through hole on the middle plate, and second pocket holes on the inner collar when the syringe is rotated to the maximum during releasing of the injector syringe.

A side, facing away from the limiting flange 101, of the clamping flange 100 is a first ramp 1001, a second ramp 600 is disposed on the inner circle of the inner collar 6, and when the clamping flange 100 pushes the inner collar 6 away, the first ramp 1001 slides along the second ramp 600, as shown in FIG. 9. In the present disclosure, the first ramp 1001 and the second ramp 600 are disposed in a manner of cooperating with each other, so that during loading, the clamping flange 100 pushes the inner collar 6 away more easily.

In this embodiment, a round through hole is disposed in the center of the middle plate 4. A diameter of the round through hole is greater than an outer diameter of the clamping flange 100, so that the clamping flange 100 passes through the middle plate 4. At the same time, the diameter of the round through hole is less than a length of a long axis of the outer circle of the limiting flange 101, so that after loading, a side of the limiting flange 101 can abut on a side of the middle plate 4 to implement limiting along an axial direction.

In this embodiment, the device for rapidly loading and releasing a syringe further includes a guide sleeve 7, used to connect the device and the injector.

Specifically, one end of the guide sleeve 7 is connected to the injection head, and the other end is connected to the injector. A guide sleeve inner hole 700 is disposed in the guide sleeve 7 along an axial direction, the guide sleeve inner hole 700 is communicated with the inner collar 6 coaxially, and the rear end of the connection end of the syringe 1 passes through the inner collar 6 and then stretches into the guide sleeve inner hole 700. Further, the guide sleeve inner hole 700 is in clearance fit with the outside (that is, an outer surface 102 of the syringe shown in FIG. 2) of the rear end of the connection end of the syringe, thereby reducing shaking of the syringe 1 in a radial direction, and ensuring stability of the connection.

The following further describes a working principle of the present disclosure, and details are follows:

1. A Loading Process

Referring to FIG. 8 to FIG. 15, the syringe 1 is inserted into the injection head 1 in any direction. After the clamping flange 100 passes through the outer collar 3 and the middle plate 4, the first ramp 1001 on the side of the clamping flange 100 abuts on the second ramp 600 on the inner circle of the inner collar 6, the syringe 1 continues to move forward and push to enable the upper part of the inner collar and the lower part of the inner collar of the inner collar to respectively move upwards and downwards, so that the clamping flange 100 passes through the inner collar 6. At the same time, the upper part of the inner collar and the lower part of the inner collar respectively move upwards and downwards to compress the elastic structures 5. In this process, due to the second pocket holes 602 disposed on the inner collar 6, space is reserved for the bosses 303 on the outer collar 4, so that the outer collar 4 remains fixed in this process.

When the side 1012 of the limiting flange 101 abuts on the side 301 of the outer collar 3, the syringe 1 is rotated in any direction until the limiting flange 101 is fit into the oval inner circle formed by the outer collar 3. After the limiting flange 101 is fit into the outer collar 3, the inner circle 301 of the outer collar 3 tightly holds the outer circle 1011 of the limiting flange 101, and the side 1012 of the limiting flange 101 abuts on the side of the middle plate 4, thereby limiting the syringe 1 in one direction along an axial direction.

After the limiting flange 101 stretches into the outer collar 3, the clamping flange 100 is disengaged from the inner collar 6, and under the action of elasticity of the elastic structures 5, the upper part of the inner collar and the lower part of the outer collar are restored to tightly hold the outer surface of the syringe 1. The inner collar 6 is located between the clamping flange 100 and the limiting flange 101. A side 1002, facing the limiting flange 101, of the clamping flange 100 is a plane, and the side 1002 abuts on the side 601 of the inner collar 6, thereby limiting the syringe 1 in the other direction along the axial direction. At the same time, the rear end of the connection end of the syringe 1 stretches into the guide sleeve inner hole 700, and is in clearance fit with the guide sleeve inner hole 700. So far, the loading process of the syringe 1 is completed.

2. A Releasing Process

Referring to FIG. 16 to FIG. 20, the syringe 1 is rotated in any direction. The major semi axis of the limiting flange 101 pushes to enable the upper part of the outer collar and the lower part of the outer collar to respectively move upwards and downwards. When the upper part of the outer collar moves upwards and the lower part of the outer collar moves downwards, outer plane 3031 of the bosses 303 abut on outer plane 6021 of the second pocket holes 602, to drive the upper part of the inner collar to move upwards and the lower part of the outer collar to move downwards, so that the inner collar 6 is separated, and the elastic structures 5 are compressed again.

After the inner collar 6 is separated, the side 1002 of the inner collar 6 is disengaged from the side 601 of the inner collar 6, and the syringe 1 is pulled outwards along an axial direction, so that the syringe 1 is released.

After the syringe 1 is released, under the elasticity of the elastic structures 5, the inner collar 6 is restored, and the outer collar 3 is restored by means of driving by the bosses 303, facilitating subsequent use.

Embodiment 2

Figure 2:
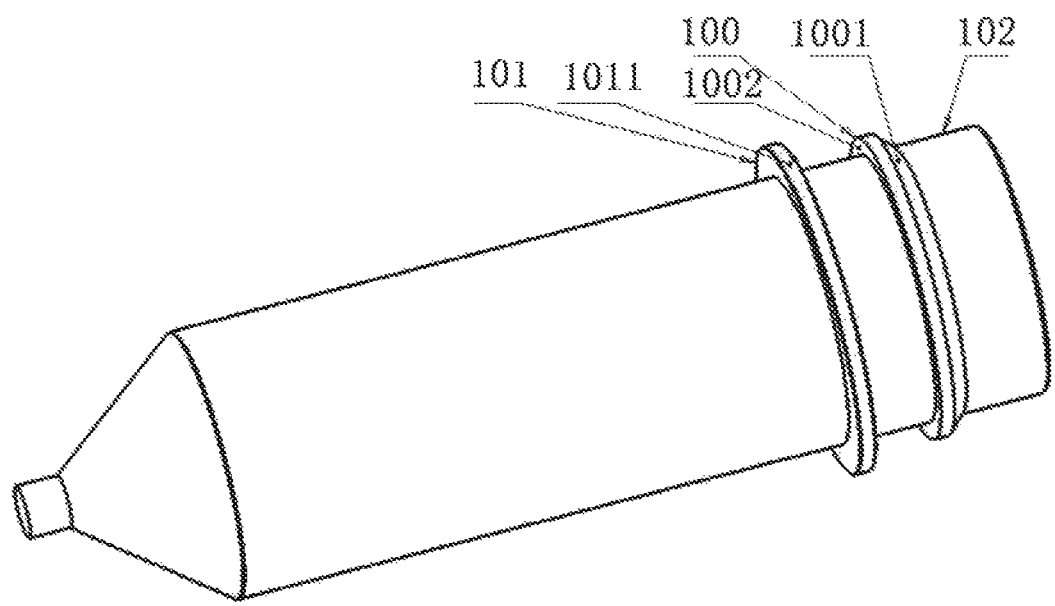
FIG. 2 is a schematic structural diagram of an injector syringe in the present disclosure.
Figure 3:
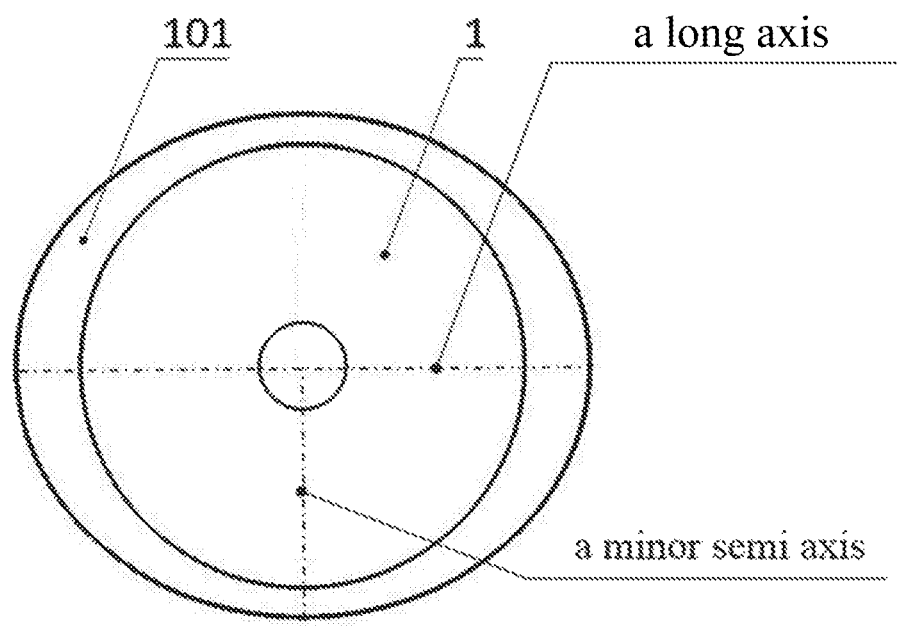
FIG. 3 is a front view of the injector syringe in FIG. 2.
Figure 4:
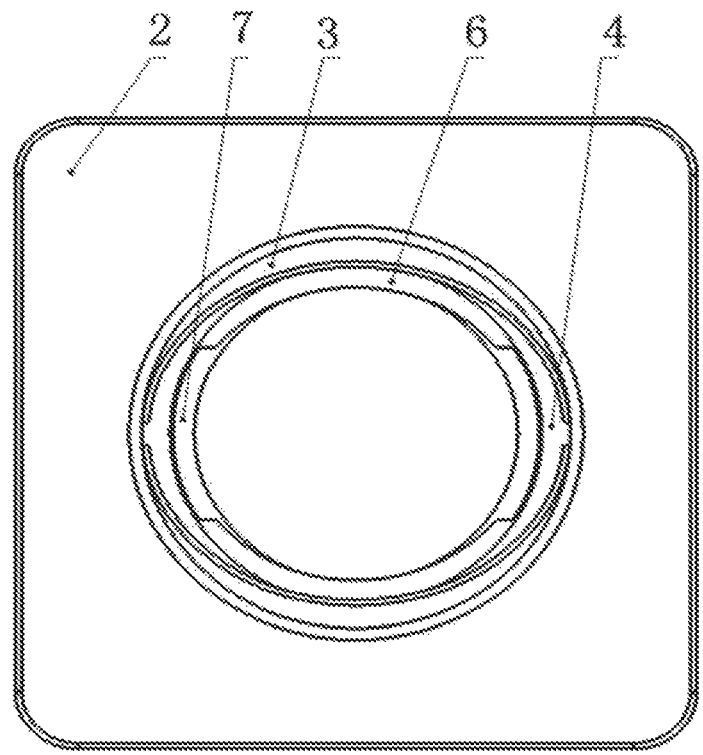
FIG. 4 is a schematic structural diagram of a device for rapidly loading and releasing a syringe provided in the present disclosure.

As shown in FIG. 2, the present disclosure further provides a syringe. The limiting flange 101 and the clamping flange 100 are disposed on an outer side wall of an end, connected to an injector, of the syringe. The clamping flange 100 is close to a rear end of the connection end of the syringe, and an outer circle of the limiting flange 101 is of an oval shape.

The syringe is connected to the injector by means of a rapid loading and releasing device. The rapid loading and releasing device is directly installed onto the injector. The syringe is loaded onto or released from the device by means of the limiting flange and the clamping flange.

The device further includes an injection head. An outer collar, a middle plate, and an inner collar are sequentially disposed inside the injection head. The outer collar includes an upper part of the outer collar and a lower part of the outer collar disposed up and down. The inner collar includes an upper part of the inner collar and a lower part of the inner collar that are disposed up and down, and elastic structures are separately disposed between the upper part of the inner collar and the injection head and between the lower part of the inner collar and the injection head. The clamping flange on the syringe is used to cooperate with the inner collar, so that after the syringe is loaded, the syringe is fixed. The limiting flange is used to cooperate with the middle plate, to limit the syringe along an axial direction after the syringe is loaded. The limiting flange 101 cooperates with the outer collar by means of an oval outer circle, so that the syringe is released rapidly.

Specifically, during loading, the syringe is inserted into the injection head. The clamping flange passes through the outer collar and the middle plate, and then pushes the inner collar away, so that the upper part of the inner collar moves upwards and the lower part of the inner collar moves downwards. After the clamping flange passes through the inner collar, under the action of the elastic structures, the upper part of the inner collar and the lower part of the inner collar are restored, a side of the clamping flange abuts on a side of the inner collar, and a side of the limiting flange abuts on a side of the middle plate, so that the syringe is positioned along the axial direction. In this case, the upper part of the outer collar and the lower part of the outer collar are fixed. An inner circle of the outer collar formed by the upper part of the outer collar and the lower part of the outer collar is of an oval shape matching the outer circle of the limiting flange, and the limiting flange is fit into the oval inner circle of the outer collar.

During releasing, the syringe is rotated, the limiting flange pushes to enable the upper part of the outer collar and the lower part of the outer collar to respectively move upwards and downwards, the upper part of the outer collar and the lower part of the outer collar respectively drive, by means of connection pieces, the upper part of the inner collar and the lower part of the inner collar to move upwards and downwards. The inner collar is opened. The clamping flange is moved outwards to be disengaged from the inner collar, so that the syringe is released. At the same time, the limiting flange is disengaged from the outer collar. Under the action of the elastic structures, the inner collar and the outer collar are restored.

In this embodiment, a side, facing away from the limiting flange, of the clamping flange is a ramp, facilitating separation of the inner collar.

A person skilled in the art should understand that the present disclosure may be implemented in many other specific forms without departing from the spirit or scope thereof. Although embodiments of the present disclosure have been described, it should be understood that the present disclosure is not limited to these embodiments. A person skilled in the art may make changes and modifications within the spirit and scope of the present disclosure that are defined in the claims.

The invention claimed is:

1. A device for rapidly loading and releasing a syringe, wherein:
   a limiting flange and a clamping flange are disposed on an outer side wall of a connection end of a syringe, the clamping flange is close to a rear end of the connection end of the syringe, and an outer circle of the limiting flange is of an oval shape;
   the device includes an injection head, an outer collar, a middle plate, and an inner collar which are disposed sequentially inside the injection head; the outer collar includes an upper part of the outer collar and a lower part of the outer collar that are disposed up and down; the inner collar includes an upper part of the inner collar and a lower part of the inner collar that are disposed up and down, and elastic structures are disposed between the upper part of the inner collar and the injection head and between the lower part of the inner collar and the injection head;
   during loading, the syringe is inserted into the injection head, the clamping flange passes through the outer collar and the middle plate and then pushes the inner collar away, the upper part of the inner collar moves upwards, and the lower part of the inner collar moves downwards; after the clamping flange passes through the inner collar, under the action of the elastic structures, the upper part of the inner collar and the lower part of the inner collar are restored, a side of the clamping flange abuts on a side of the inner collar, and a side of the limiting flange abuts on the middle plate, so that the syringe is positioned along an axial direction; the upper part of the outer collar and the lower part of the outer collar are fixed, an inner circle of the outer collar formed by the upper part of the outer collar and the lower part of the outer collar is of an oval shape matching the outer circle of the limiting flange, and the limiting flange is fit into the oval-shaped inner circle of the outer collar; and
   during releasing, the syringe is rotated, the limiting flange pushes to enable the upper part of the outer collar and the lower part of the outer collar to respectively move upwards and downwards, the upper part of the outer collar and the lower part of the outer collar respectively drive, by means of connection pieces, the upper part of the inner collar and the lower part of the inner collar to move upwards and downwards; the inner collar is opened, the clamping flange is moved outwards to be disengaged from the inner collar, to release the syringe; at the same time, the limiting flange is disengaged from the outer collar, and under the action of the elastic structures, the inner collar and the outer collar are restored, wherein the connection pieces comprise bosses disposed on sides, facing the middle plate, of the upper part of the outer collar and the lower part of the outer collar, first pocket holes are disposed on corresponding locations on the middle plate, second pocket holes are disposed on corresponding locations on the upper part of the inner collar and the lower part of the inner collar, the bosses pass through the first pocket holes and the second pocket holes, and the bosses can move upwards and downwards relative to the first pocket holes and the second pocket holes.

2. The device for rapidly loading and releasing a syringe according to claim 1, wherein a difference between a major semi axis and a minor semi axis of the outer circle of the limiting flange is greater than a movable distance of the upper part of the outer collar and the lower part of the outer collar.

3. The device for rapidly loading and releasing a syringe according to claim 1, wherein a side, facing away from the limiting flange, of the clamping flange is a first ramp, a second ramp is disposed on an inner circle of the inner collar, and when the clamping flange pushes the inner collar away, the first ramp slides along the second ramp.

4. The device for rapidly loading and releasing a syringe according to claim 1, wherein a chamfer is disposed on a side, facing away from the middle plate, of the inner circle of the outer collar.

5. The device for rapidly loading and releasing a syringe according to claim 1, wherein before loading, the bosses are close to inner sides of the first pocket holes and close to outer sides of the second pocket holes.

6. The device for rapidly loading and releasing a syringe according to claim 1, wherein an outer circle of the clamping flange is round.

7. The device for rapidly loading and releasing a syringe according to claim 1, wherein a round through hole is disposed at the center of the middle plate, a diameter of the round through hole is greater than an outer diameter of the clamping flange, and is less than a length of a long axis of the outer circle of the limiting flange.

8. The device for rapidly loading and releasing a syringe according to claim 1, wherein a limiting step hole is disposed on a side, facing the syringe, of the injection head, a slot communicating with the limiting step hole is disposed on an other side, and the outer collar, the middle plate, and the inner collar are installed inside the slot.

9. The device for rapidly loading and releasing a syringe according to claim 1, further comprising a guide sleeve, used to implement connection between the device for rapidly loading and releasing a syringe and an injector.

10. The device for rapidly loading and releasing a syringe according to claim 9, wherein one end of the guide sleeve is connected to the injection head, the other end is connected to the injector; a guide sleeve inner hole is disposed on the guide sleeve along an axial direction, the guide sleeve inner hole is communicating with the inner collar, and the rear end of the connection end of the syringe passes through the inner collar and then stretches into the guide sleeve inner hole.

11. The device for rapidly loading and releasing a syringe according to claim 10, wherein the guide sleeve inner hole is in clearance fit with an outside of the rear end of the connection end of the syringe.

12. An assembly comprising the device for rapidly loading and releasing the syringe of claim 1, and a syringe.

13. The assembly according to claim 12, wherein a side, facing away from the limiting flange, of the clamping flange is a ramp.

* * * * *